US00PP14436P39

(12) United States Plant Patent
Davidson, Jr.

(10) Patent No.: US PP14,436 P3
(45) Date of Patent: Dec. 30, 2003

(54) BERMUDA GRASS NAMED 'MACHO WORLD FEEDER'

(50) Latin Name: *Cynodon dactylon (L.)*
Varietal Denomination: Macho World Feeder

(75) Inventor: David C. Davidson, Jr., Poteet, TX (US)

(73) Assignee: DavGor, Limited, Poteet, TX (US)

( * ) Notice: Subject to any disclaimer, the term of this patent is extended or adjusted under 35 U.S.C. 154(b) by 0 days.

(21) Appl. No.: 10/062,726

(22) Filed: Feb. 5, 2002

(65) Prior Publication Data

US 2003/0150040 P1 Aug. 7, 2003

(51) Int. Cl.[7] ..... A01H 5/00

(52) U.S. Cl. ..... Plt./389

(58) Field of Search ..... Plt./389

*Primary Examiner*—Bruce R. Campell

*Assistant Examiner*—Annette Para

(74) *Attorney, Agent, or Firm*—Jondle & Associates, PC

(57) ABSTRACT

This invention relates to a new and distinct Bermuda grass (*Cynodon dactylon*) designated 'Macho World Feeder' which is outstanding because of its 1) aggressive growth; 2) its excellent feed values; 3) its salt tolerance; and 4) its drought resistance.

5 Drawing Sheets

Genus and species: Bermuda grass (*Cynodon dactylon* (L.)).

BACKGROUND

'Macho World Feeder' is a new and distinct cultivar of Bermuda grass which is developed for forage grass and turfgrass. An important characteristic of a forage grass is that it is good tasting to animals and nutritious by providing most or all the animals dietary needs.

SUMMARY OF THE INVENTION

This invention relates to a new and distinct Bermuda grass (*Cynodon dactylon*) designated 'Macho World Feeder' which is outstanding because of its 1) aggressive growth; 2) its excellent feed values; 3) its salt tolerance; and 4) its drought resistance. The claimed Bermuda grass 'Macho World Feeder' was primarily selected for these characteristics.

The present invention is a mutant that was discovered in August, 2000 after the inventor noticed an area of grass which was distinctly taller and larger-leafed and stemmed than the surrounding grass which was 'World Feeder' Bermuda Grass (U.S. Plant Pat. No. 7,081). The grass was selected, separated and propagated during September and October. Asexual reproduction of the grass by vegetative propagation in Poteet, Tex. confirmed that the plant does in fact maintain the characteristics described through successive propagations.

DEFINITIONS

In the description and tables which follow, a number of terms are used. In order to provide a clear and consistent understanding of the specification and claims, including the scope to be given such terms, the following definitions are provided:

Total Digestible Nutrients (TDN)—As used herein, the term "total digestible nutrients" is a measurement of the energy value of a feed or forage grass.

Acid Detergent Fiber (ADF)—As used herein, the term "acid detergent fiber" is a measurement of lignin and cellulose fiber content of a feed or forage which helps determine its digestibility. The desired range is between 28%–32%.

ORIGIN AND ASEXUAL REPRODUCTION

Asexual reproduction of this turfgrass by vegetative propagation was directed by me, such reproduction establishing that the plant is stable and in fact maintain the characteristics described, in successive generations.

BRIEF DESCRIPTION OF THE DRAWINGS

The accompanying photographs show as nearly true as it is reasonably possible to make the same, in color illustrations of this character, the new variety. All comparisons in these photographs were from samples that were planted at the same time and with identical environmental conditions.

DETAILED DESCRIPTION OF THE INVENTION

Figure 1:
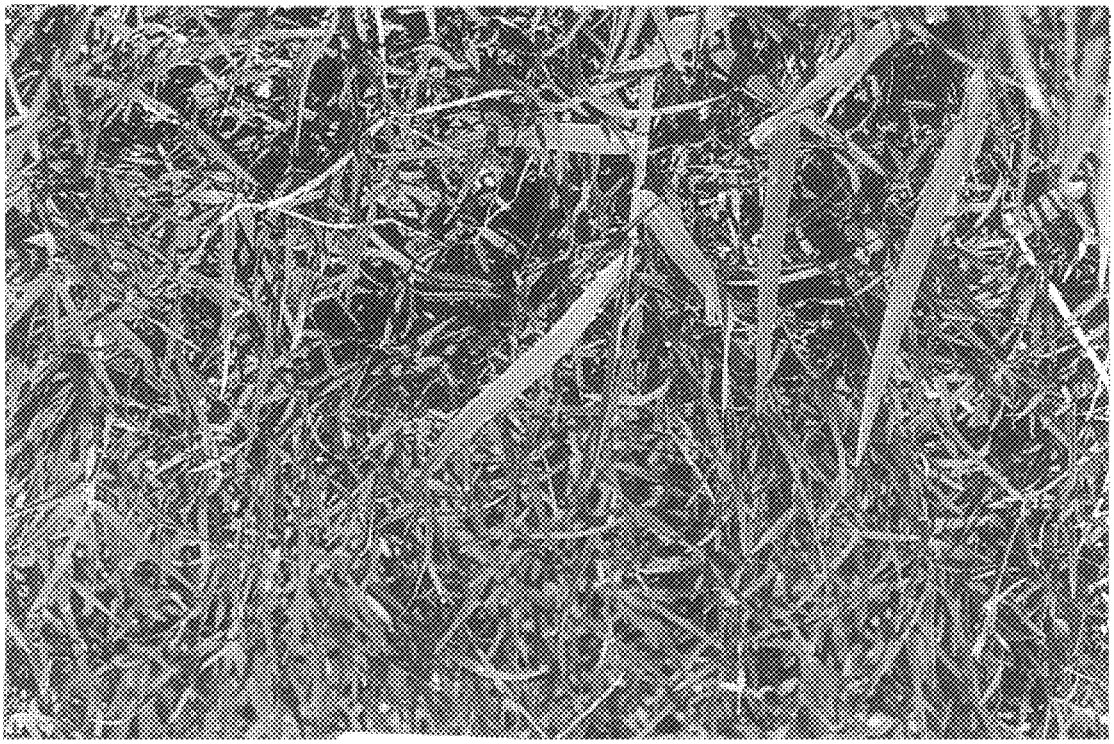
FIG. 1 shows 'Macho World Feeder' Bermuda grass growing in a field next to the parental cultivar 'World Feeder' Bermuda Grass (U.S. Plant Pat. No. 7,081).
Figure 2:
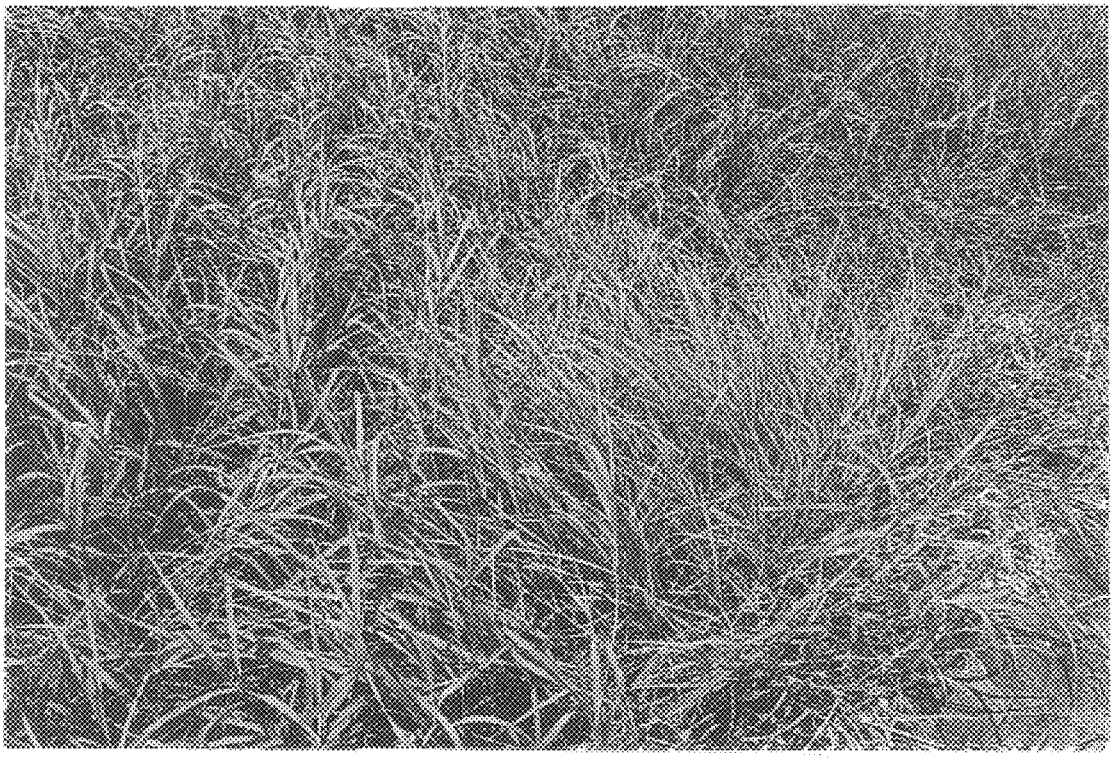
FIG. 2 shows 'Macho World Feeder' Bermuda grass growing in a field next to 'Coastal' Bermuda grass.
Figure 3:
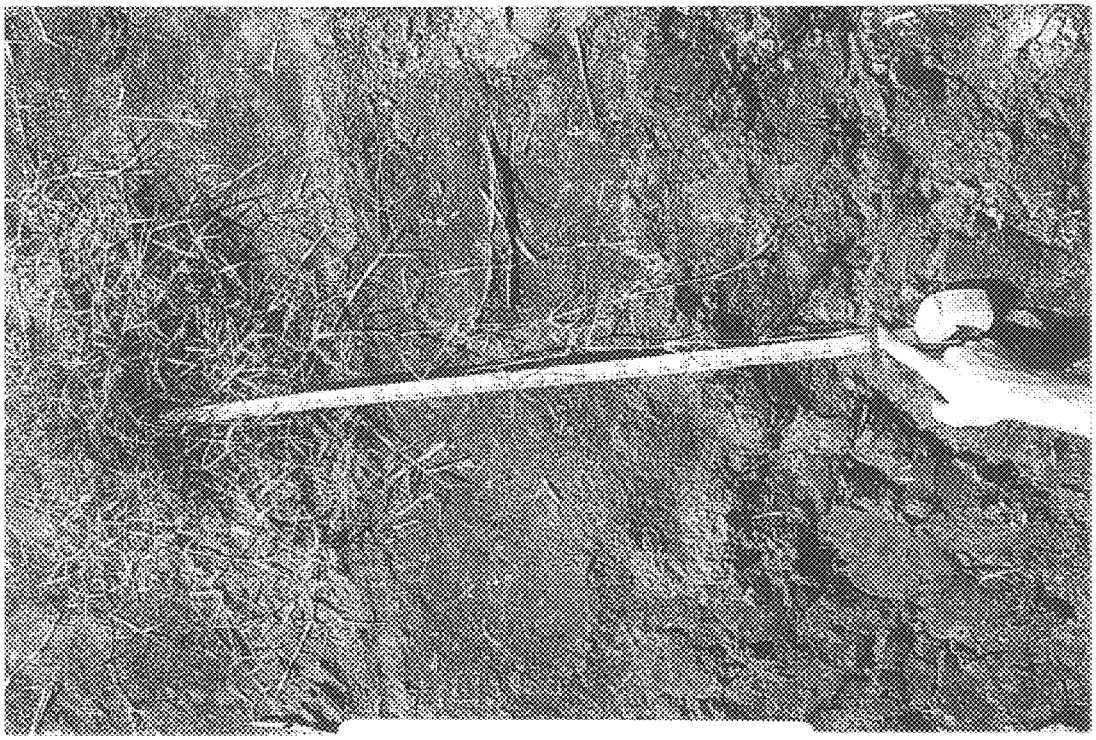
FIG. 3 and FIG. 3A show measurements of stolons from 'Macho World Feeder' Bermuda grass and parental cultivar 'World Feeder' Bermuda Grass respectively.
Figure 3A:
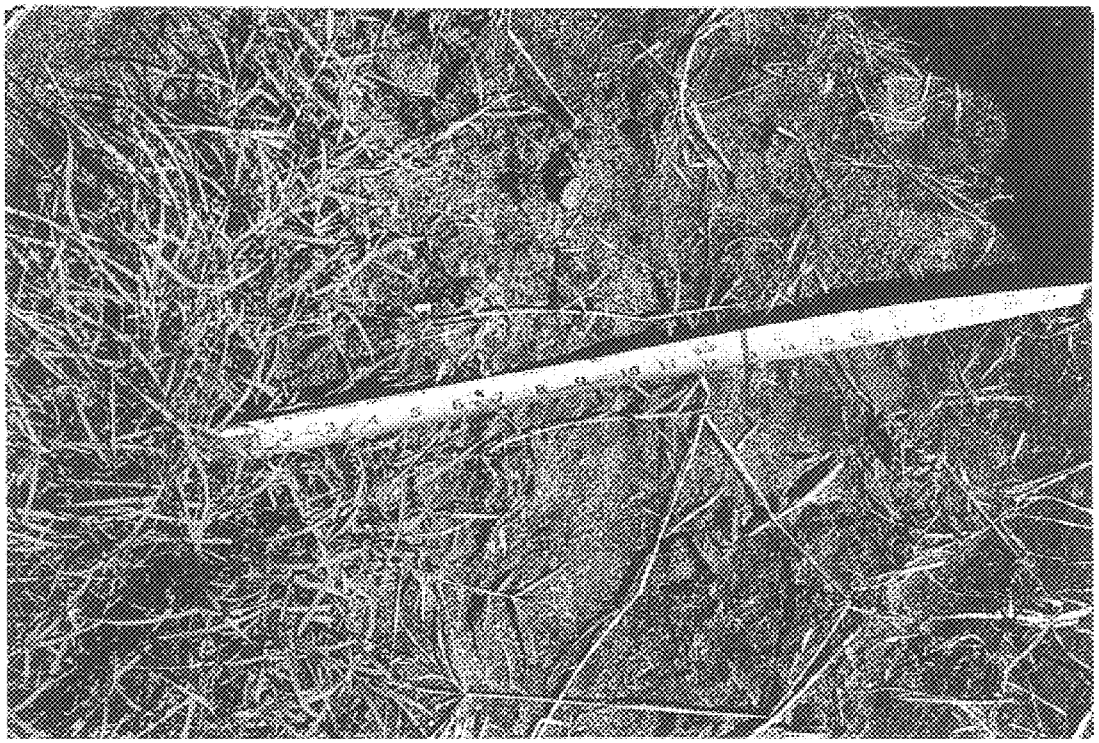
Figure 4:
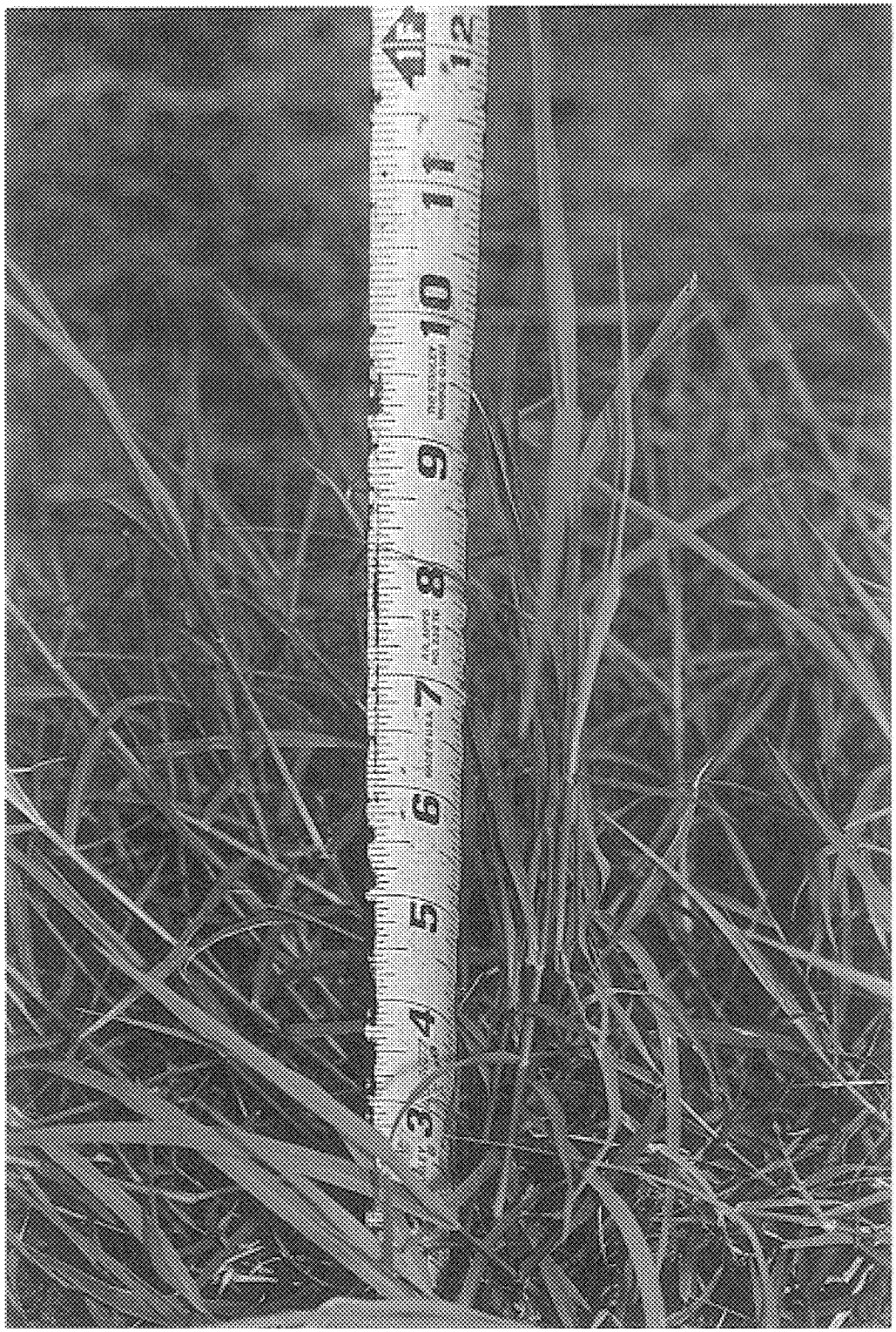
FIG. 4 and FIG. 4A show vertical growth of 'Macho World Feeder' and 'World Feeder' Bermuda Grass respectively.
Figure 4A:
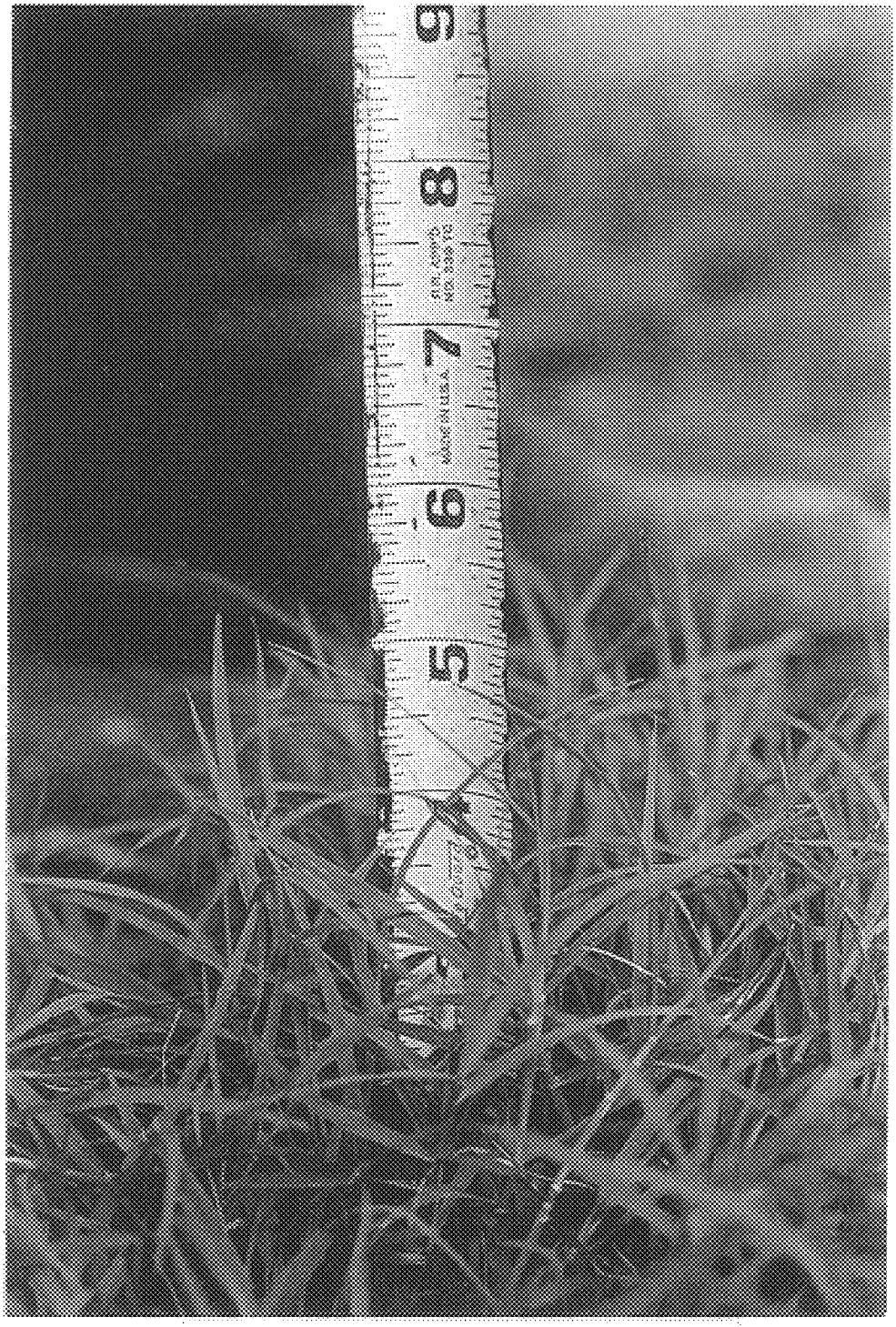
Figure 5:
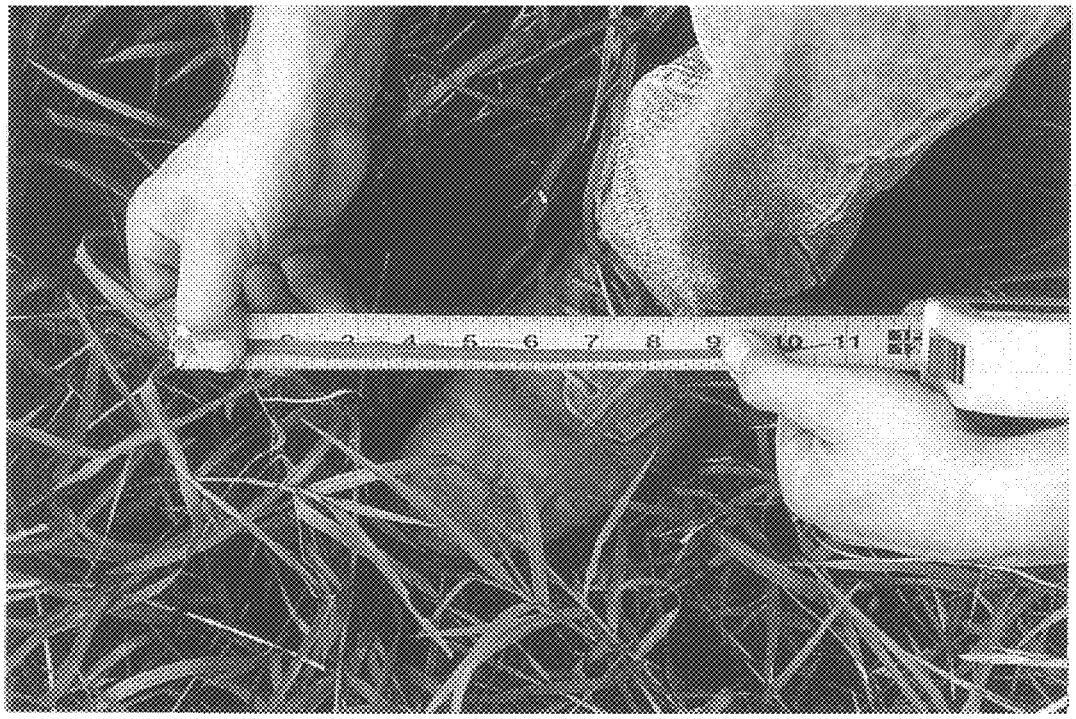
FIG. 5 and FIG. 5A show the blade length of 'Macho World Feeder' and 'World Feeder' Bermuda Grass respectively.
Figure 5A:
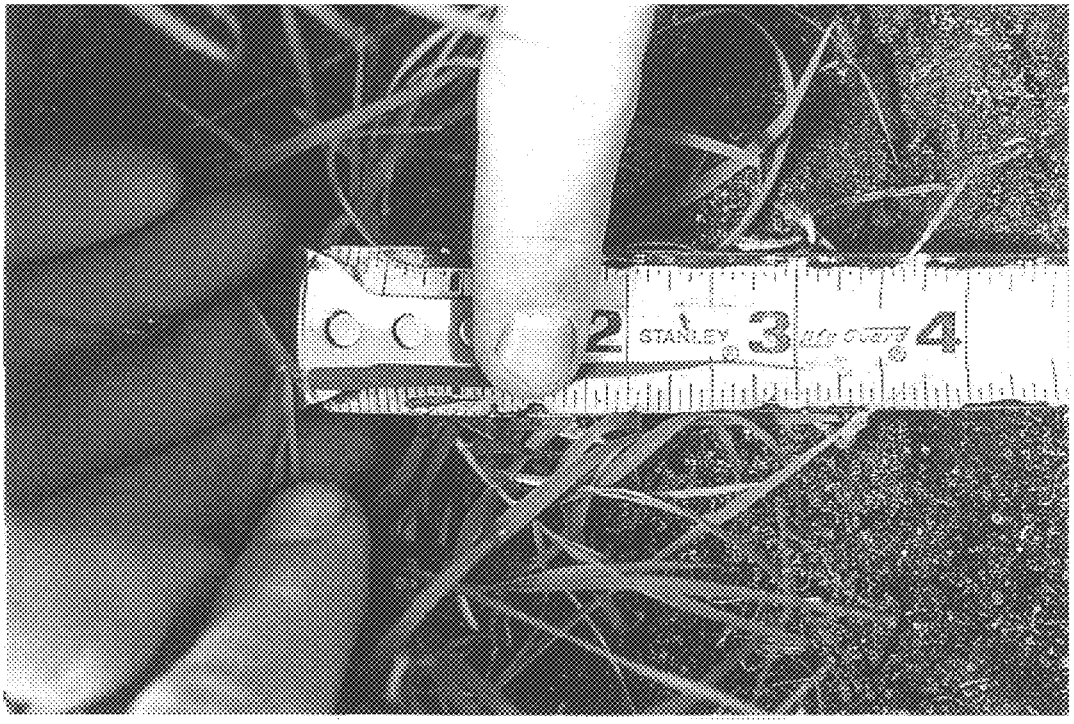

The following description is based on observations and measurements from plants that were approximately 6 months old in Poteet, Tex. Color references are primarily to the Munsell Color Charts for Plant Tissue.

Parentage: 'World Feeder' Bermuda Grass (U.S. Plant Pat. No. 7,081).

Propagation: Vegetative cuttings or sod.

Growth habit:

*Stolons.*—Stem distance between nodes: Average 14.8 cm on horizontal stolons; width of stolon is 2–3 mm; daily growth over 3 day period is 9 cm.

*Leaves.*—This high quality grass is medium rich green (RHS 5G 7/6) in color. The leaf blades are soft with a medium-fine texture. Leaf width averages 4–5 mm; leaf length averages 17 cm with several being 26–30 cm; leaf veins are obscure and margins are serrated.

Observations: This sterile hybrid establishes quickly by stolons and rhizomes, grows vigorously and spreads aggressively. The stems had very little lignification thus producing a higher feeding value forage as it contains more protein and requires less energy for consumption. The parent plant seed spikes measured 3.5 cm–8.5 cm in length and had 6–7 seed stems in a "star shaped" whorl. Seed produced is very soft, ovoid shaped and light tan (2.5Y 6/4) with a darker tan (2.5Y 5/2) line at the base. The majority of the seeds are not intact and their edges are feathered. Seeds range in size from 33.25 mm–4.50 mm in length by 1 mm in width.

Grass grew approximately 15–16 inches over a 5-day period in the spring.

*Cold tolerant.*—Survived Texas and Oklahoma winters; further testing in Nebraska and Iowa.

*Salt tolerant.*—'Macho World Feeder' has survived 30,000 parts per million salt through two cutting cycles.

The grass is medium rich emerald green (5G 7/6) at the lower surface and lighter emerald green (7.5GY 4/4) (taking a very slight yellowish tinge) at the upper portion. Many of the blades observed had a purplish (5RP 4/2) hue at the stem base, the lower 3–6 cm, which indicates good nitrogen content.

The culms observed ranged 85.5 cm–92.1 cm in length from tip of the seed star stem to the very end tip of the longest root. The widest part of the culms was the rhizomes which measurements ranged from 16.5 cm–18 cm in width. The grass stems measured 54.5 cm–60 cm in length and the rhizomes 31.0–32.5 cm in length. The leaf blades were 1.8 mm–2.0 mm in width and the rhizomes lateral shoots measured 16.5 cm–18 cm in width. The color was the same as observed in the field.

Feed values:

At premium harvest age, protein levels of 26.8% have been obtained. A sample taken 10 days later measured 22.4% protein and a sample that was allowed to head out still measured 22% protein. Total digestible nutrients (TDN) measured from 68.6% to 72.6% and acid detergent fiber (ADF) measured from 26.3% to 29.8%.

One plot was allowed to grow uncut from early March to July 10. The protein was still 10.8%, ADF 38.7% and TDN 58.4%.

Comparison with parental cultivar:

'Macho World Feeder' grows approximately 300–400% faster than 'World Feeder' Bermuda grass (U.S. Plant Pat. No. 7,081). The leaf blades and stolons are much larger than 'World Feeder'. Additionally, 'Macho World Feeder' has a higher protein percent over 'World Feeder' Bermuda Grass.

When 'Macho World Feeder' is compared to coastal Bermuda, 'Macho World Feeder' is higher in quality, richer green in color, established quicker, had a sturdier root system and the seed spikes were longer and had more seed stems in each whorl.

Plant disease—drought resistance:

'Macho World Feeder' is very drought resistant and can tolerate long periods of flooding. This grass enters dormancy when temperatures drop below 45° F. (7.28° C.) and recovers quickly when temperatures begin to rise.

No plant diseases have been observed. The grass is susceptible to armyworms and grasshoppers.

What is claimed is:

1. A new and distinct Bermuda Grass plant as described and illustrated herein.

* * * * *